(12) United States Patent
Moore (10) Patent No.: US 7,686,843 B2
(45) Date of Patent: *Mar. 30, 2010

(54) FLEXIBLE AND CONFORMABLE STENT

(75) Inventor: Brian E. Moore, Sunnyvale, CA (US)

(73) Assignee: Unison Therapeutics, Inc., Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/399,862

(22) Filed: Apr. 7, 2006

(65) Prior Publication Data

US 2006/0184233 A1    Aug. 17, 2006

Related U.S. Application Data

(63) Continuation of application No. 10/210,448, filed on Jul. 31, 2002, now Pat. No. 7,025,777.

(51) Int. Cl.
 *A61F 2/06* (2006.01)
(52) U.S. Cl. .................. 623/1.16; 623/1.15; 623/1.17
(58) Field of Classification Search ............. 623/1.15, 623/1.16, 1.17, 1.18
See application file for complete search history.

(56) References Cited

U.S. PATENT DOCUMENTS

| | | | |
|---|---|---|---|
| 4,733,665 A | 3/1988 | Palmaz | |
| 4,739,762 A | 4/1988 | Palmaz | |
| 4,800,882 A | 1/1989 | Gianturco | |
| 4,907,336 A | 3/1990 | Gianturco | |
| 5,035,706 A | 7/1991 | Gianturco et al. | |
| 5,037,392 A | 8/1991 | Hillstead | |
| 5,041,126 A | 8/1991 | Gianturco | |

(Continued)

FOREIGN PATENT DOCUMENTS

DE    199 36 483 A1    2/2001

(Continued)

OTHER PUBLICATIONS

Bellouard, Y. et al., "Local annealing of complex mechanical devices: a new approach for developing monolithic micro-devices," *Materials Science and Engineering* A273-275, pp. 795-798 (1999).

(Continued)

*Primary Examiner*—Bruce E Snow
(74) *Attorney, Agent, or Firm*—Haynes & Boone LLP (57) ABSTRACT

An expandable stent is fabricated from a plurality of radially undulating rings, each pair of adjacent radially expandable undulating rings being interconnected by a multiplicity of flex members. Each flex member contacts a portion of an apex on one ring at a circumferential location and a portion of an apex of a directly adjacent ring at a circumferentially offset location. Each flex member is expandable and in one embodiment is circumferentially S-shaped. Adjacent flex members are mirror images of each other. The resulting stent is both flexible and strong when expanded thereby providing good scaffolding. In one embodiment, the strut material is fabricated of shape memory alloy such that when the strut is compressed so as to be insertable into a vessel, the strut will automatically expand to its previous dimension upon rising to the temperature of the vessel in which it is placed, thereby to expand and hold open the vessel without need for a balloon catheter.

41 Claims, 10 Drawing Sheets

U.S. PATENT DOCUMENTS

| | | | |
|---|---|---|---|
| 5,102,417 A | 4/1992 | Palmaz | |
| 5,147,385 A | 9/1992 | Beck et al. | |
| 5,282,824 A | 2/1994 | Gianturco | |
| 5,316,023 A | 5/1994 | Palmaz et al. | |
| 5,697,971 A | 12/1997 | Fischell et al. | |
| 5,755,771 A | 5/1998 | Penn et al. | |
| 5,911,754 A | 6/1999 | Kanesaka et al. | |
| 6,017,365 A | 1/2000 | Von Oepen | |
| 6,066,169 A | 5/2000 | McGuinness | |
| 6,146,417 A | 11/2000 | Ischinger | |
| 6,183,506 B1 | 2/2001 | Penn et al. | |
| 6,190,403 B1 | 2/2001 | Fischell et al. | |
| 6,217,608 B1 | 4/2001 | Penn et al. | |
| 6,334,870 B1 | 1/2002 | Ehr et al. | |
| 6,375,677 B1 | 4/2002 | Penn et al. | |
| 6,511,505 B2 | 1/2003 | Cox et al. | |
| 6,565,598 B1 | 5/2003 | Lootz | |
| 6,602,282 B1 | 8/2003 | Yan | |
| 6,602,284 B2 * | 8/2003 | Cox et al. | 623/1.15 |
| 6,629,994 B2 | 10/2003 | Gomez et al. | |
| 7,025,777 B2 * | 4/2006 | Moore | 623/1.15 |
| 2006/0142849 A1 * | 6/2006 | Killion et al. | 623/1.31 |
| 2006/0178724 A1 * | 8/2006 | Pinchasik et al. | 623/1.15 |

FOREIGN PATENT DOCUMENTS

| | | |
|---|---|---|
| EP | 1 129 673 A2 | 9/2001 |
| JP | 10-52503 | 2/1998 |
| WO | WO 00/35378 | 6/2000 |

OTHER PUBLICATIONS

Bellouard, Y. et al., "Laser annealing of shape memory alloys: A versatile tool for developing smart micro-devices," *J. Physics IV France* 11, pp. Pr8-571-Pr8-576 (6 pages) (2001).

Dunitz, Martin, *Handbook of Coronary Stents*, Fourth Edition, © Martin Dunitz Ltd 2002, First Published in the United Kingdom in 1997 by Martin Dunitz Ltd, The Livery House, 7-9 Pratt Street, London NW1 0AE.

Dunitz, Martin, *Handbook of Coronary Stents*, Fourth Edition, © Martin Dunitz Ltd 2002, First Published in the United Kingdom in 1997 by Martin Dunitz Ltd, The Livery House, 7-9 Pratt Street, London NW1 0AE, pp. 109-116.

Dunitz, Martin, *Handbook of Coronary Stents*, Fourth Edition, © Martin Dunitz Ltd 2002, First Published in the United Kingdom in 1997 by Martin Dunitz Ltd, The Livery House, 7-9 Pratt Street, London NW1 0AE, pp. 226, 227.

Hafez, M. et al., "Local annealing of shape memory alloys using laser scanning and computer vision," First International Symposium on Laser Precision Microfabrication, Miyamoto et al., Editors, *Proceedings of SPIE* vol. 4088 © 2000 SPIE 0277-788x00 94; pp. 160-163 (2000).

* cited by examiner

DIST FROM LEAST- SUPPORTED POINT TO NEAREST EDGE

Pk. 0.0254

FLEXIBLE AND CONFORMABLE STENT

CROSS-REFERENCE TO RELATED APPLICATION

This application is a continuation of U.S. patent application Ser. No. 10/210,448, filed Jul. 31, 2002, now U.S. Pat. No. 7,025,777 by Brian E. Moore for "FLEXIBLE AND CONFORMABLE STENT AND METHOD OF FORMING SAME", the contents by which are incorporated herein by reference in their entirety.

FIELD OF THE INVENTION

The present invention relates to an expandable stent.

BACKGROUND OF THE INVENTION

Description of the Prior Art

Stents are generally known. Indeed, the term "stent" has been used interchangeably with terms such as "intraluminal vascular graft" and "expansible prosthesis". As used throughout this specification the term "stent" is intended to have a broad meaning and encompasses any expandable prosthetic device for implantation in a body passageway (e.g., a lumen or artery).

In the past fifteen years, the use of stents has attracted an increasing amount of attention due the potential of these devices to be used, in certain cases, as an alternative to surgery. Generally, a stent is used to obtain and maintain the patency of the body passageway while maintaining the integrity of the passageway. As used in this specification, the term "body passageway" is intended to have a broad meaning and encompasses any duct (e.g., natural or iatrogenic) within the human body and can include a member selected from the group comprising: blood vessels, respiratory ducts, gastrointestinal ducts and the like.

Stent development has evolved to the point where the vast majority of currently available stents rely on controlled plastic deformation of the entire structure of the stent at the target body passageway so that only 'sufficient force to maintain the patency of the body passageway is applied during expansion of the stent.

Generally, in many of these systems, a stent, in association with a balloon, is delivered to the target area of the body passageway by a catheter system. Once the stent has been properly located (for example, for intravascular implantation, the target area of the vessel can be filled with a contrast medium to facilitate visualization during fluoroscopy), the balloon is expanded thereby plastically deforming the entire structure of the stent so that the latter is urged in place against the body passageway. As indicated above, the amount of force applied is at least that necessary to expand the stent (i.e., the applied force exceeds the minimum force above which the stent material will undergo plastic deformation) while maintaining the patency of the body passageway. At this point, the balloon is deflated and withdrawn into the guide catheter, and is subsequently removed. Ideally, the stent will remain in place and maintain the target area of the body, passageway substantially free of blockage (or narrowing).

See, for example, any of the following patents:
U.S. Pat. No. 4,733,665 (Palmaz),
U.S. Pat. No. 4,739,762 (Palmaz),
U.S. Pat. No. 4,800,882 (Gianturco),
U.S. Pat. No. 4,907,336 (Gianturco),
U.S. Pat. No. 5,035,706 (Gianturco et al.)
U.S. Pat. No. 5,037,392 (Hillstead),
U.S. Pat. No. 5,041,126 (Gianturco),
U.S. Pat. No. 5,102,417 (Palmaz),
U.S. Pat. No. 5,147,385 (Beck et al.),
U.S. Pat. No. 5,282,824 (Gianturco),
U.S. Pat. No. 5,316,023 (Palmaz et al.),
U.S. Pat. No. 5,755,771 (Penn et al.),
U.S. Pat. No. 6,183,506 (Penn et al.), and
U.S. Pat. No. 6,217,608 (Penn et al.), for a discussion of previous stent designs and deployment systems. See also the book entitled "Handbook of Coronary Stents" Fourth Edition, edited by Serruys and Rensing, copyright 2002, Martin Dunitz Ltd., for a description on pages 109 to 116 of the prior art Genius Coronary Stent using two S shaped circumferentially oriented links to connect two adjacent expandable undulating rings.

Two of the functional constraints which govern the usefulness of a stent are first, the stent should have a high degree of flexibility in the unexpanded state to facilitate navigation of the stent through tortuous anatomy to the location of the target stenosis and second, the expanded stent should be radially rigid to minimize the effects of restenosis and the possibility of acute occlusion. Thus, an ideal stent would be characterized by certain functional properties (i.e., flexibility and dimensional stability) independent of the state of the stent (i.e., expanded or unexpanded).

Prior art stents often achieve flexibility at the expense of the ability to support radially the vessel wall and to deliver medicines or drugs uniformly to the vessel wall. Moreover, such stents, when expanded, often lose flexibility and conformability.

Accordingly, it would be desirable to have an improved stent which overcomes these disadvantages (i.e., improved radial support, improved uniformity of drug delivery, improved flexibility during delivery, and improved conformability) can be manufactured readily, and can be deployed using conventional stent delivery systems.

SUMMARY OF THE INVENTION

The present invention obviates or mitigates at least some of the above-mentioned has disadvantages of the prior art.

Accordingly, in one of its aspects, the present invention provides an unexpanded stent comprising: a plurality of radially expandable undulating rings, each radially expandable undulating ring comprising a strut with a plurality of apices; a plurality of arcuate flex members connecting adjacent first and second radially expandable undulating rings; the first radially expandable undulating ring comprises a strut with more than one complete sinusoidal cycle which is coupled to two circumferentially adjacent arcuate flex members; and the second radially expandable undulating ring comprises a strut with less than one complete sinusoidal cycle which is coupled to two circumferentially adjacent arcuate flex members.

In another of its aspects, the present invention provides a stent comprising: a first radially expandable undulating ring comprising a first apex; a second radially expandable undulating ring comprising a second apex longitudinally unaligned with respect to the first apex; and a mirrored pair of arcuate flex members interconnecting the first ring and the second ring.

According to another aspect, the present intervention provides a stent comprising:

a first radially expandable undulating ring comprising a first apex and a second apex; a second radially expandable undulating ring comprising a third apex and a fourth apex circumferentially offset with respect to the first and second apices; a mirrored pair of first and second flex members wherein the first flex member is connected to the first apex at a first connection location and to the third apex at a third connection location, and the second flex member is connected to the second apex at a second connection location and to the fourth apex at a fourth connection location; wherein there is no further connection of the first radially expandable undulating ring to the second radially expandable undulating ring along a shortest path length on the first radially expandable undulating ring between the first connection location and the second connection location; and further wherein there is no further connection of the second radially expandable undulating ring to the first radially expandable undulating ring along a shortest path length on the second radially expandable undulating ring between the third connection location and the fourth connection location.

The novel stent design of this invention has several unique features. In one embodiment, more than two cycles of the radially expandable undulating struts are located adjacent one pair of arcuate flex members which connect adjacent ones of the first and second radially expandable undulating rings. The links between a pair of radially expandable undulating struts are each the mirror image of the other. While at least one prior art stent uses a longitudinal sinusoidal link, in this embodiment the invented stent utilizes circumferentially S-shaped links with adjacent-links being mirror images of each other.

One advantage of the invented stent is that over a given length of the stent there are more expansion rings and more links so the stent has greater flexibility, more even distribution of support, more uniform drug distribution and better conformability than the prior art. While the ideal stent has infinite flexibility, the invented stent has much greater flexibility than the prior art. The invented stent also has excellent scaffolding properties; i.e., the invented stent supports the blood vessels and other lumens by having a relatively uniform distribution of support structure in the expanded state. This is achieved by causing the stent to maintain a more constant distribution of the struts over the length of the stent compared to prior art stents which helps structurally support the lumen thereby to keep open the flow passage in which the stent is inserted. This feature also allows more uniform drug delivery utilizing drugs coated onto or formed with the stent material.

The bending mechanism of the invented stent differs from the bending mechanism of most prior art stents by using a circumferential rather than a longitudinal S-shape to link adjacent expansion struts. While in the prior art longitudinal S-shapes link or connect the expansion strut rings, in one embodiment the invented stent structure uses circumferentially "S" shaped arcuate flex members with adjacent flex members being mirror images of each other, to connect pairs of radially expanding undulating rings to give better pivoting. Because each circumferential "S" shaped link expands as the stent expands, stent flexibility is maintained as the stent expands.

The shape of the flex members interconnecting adjacent radially expanding undulating rings helps maintain a continuous curve during flexing of the stent while the stent is being inserted into a vessel. This greatly improves the insertability of the stent, reducing the risk of injury to the vessel. After expansion, this feature also allows the stent in its expanded state to follow the curvature of the vessel, thereby further preventing injury to the vessel. The invented structure wherein the longitudinal length of each expandable ring or strut is short (typically less than two unexpanded stent diameters), has dimensions such as to approximate a smooth curve when the stent structure is bent.

As a result, the invented stent is quite flexible (i.e., trackable) which means the invented stent has the ability to go around corners better than prior art stents. After the invented stent is expanded, the stent is longitudinally conformable to the lumen or vessel. This is important because some prior art stents while flexible when unexpanded, straighten out and stiffen up when expanded thereby attempting to straighten out the vessel in which they are placed. The circumferential S-links and the close spacing of the expansion rings both contribute to the improved flexibility and more uniform vessel support of the invented stent. This invented stent therefore combines good vessel wall support (i.e., "good scaffolding") with good flexibility.

While the prior art categorizes the stents as "closed cell" (every apex in the cell boundary is tied to another apex) or "open cell" (one or more apices in the cell boundary are not tied to another apex), the invented stent structure has advantages of both "closed" and "open" cells without their significant disadvantages.

The closed cell tends to straighten out when inserted and expanded and this is not good. In the invented stent, the link and expansion rings have the same longitudinal spatial frequency but each link contacts adjacent rings on circumferentially different longitudinal lines while some prior art links contact adjacent rings on the same longitudinal lines. In addition, each link is not directly connected to adjacent links. In one embodiment each nine expansion ring is made up of nine sinusoidally undulating struts but only six links are provided to connect adjacent expansion rings. This structure allows the invented stent to achieve better flexibility and better conformability than prior art stents.

In addition, the invented stent has more structural features around the circumference which enables each ring to be longitudinally shorter and thus gives better resolution. The longitudinally shorter stent expansion rings enable better flexibility and conformability to the vessel.

In one embodiment of the invented stent, six links are placed around the circumference and six connections are thus formed between adjacent expansion rings. Of course, other numbers of link members can also be used in the spirit of the invention.

The invented stent reduces tissue prolapse, provides more uniform support distribution (i.e., more uniform scaffolding and radial strength), and provides more uniform drug distribution. While sometimes restenosis occurs after a stent has been placed in a vessel, drug coatings delay a stent restenosis. So the material in the invented stent not only coats well with a drug but more uniformly distributes the drug than in the prior art.

BRIEF DESCRIPTION OF THE DRAWINGS

An embodiment of the present invention will be described with reference to the accompanying drawings, wherein like reference numerals denote like parts, and in which.

DETAILED DESCRIPTION OF THE PREFERRED EMBODIMENTS

Described herein is a novel stent design which has flexibility characteristics superior to currently available stent structures. Further, the expanded stent exhibits an inherent tendency to maintain the longitudinal shape of the lumen in which it is deployed. This is a significant advantage of the present stent compared to many currently available stents. Specifically, upon expansion, many currently available stents tend to stretch and straighten and thus deform the lumen along its length from its natural orientation.

Upon expansion, the repeating pattern in the present stent becomes expanded, ideally to a truss-like shape, which results in very desirable radial rigidity. Further, the present stent has a desirable strut density when expanded thereby resulting in excellent vessel coverage while allowing side branch access.

Other advantages of the present stent design will be readily apparent to those of skill in the art.

The present stent may be constructed from any suitable starting material. Preferably, the starting material is a thin-walled tube of a metal, alloy, plastic or polymer. Alternatively, it is possible to construct the present stent from a flat sheet which preferably is cut to form a rectangle with two parallel long sides, (as described below), rolled until the two long sides abut and then welded.

In one preferred embodiment, the starting material may be one which is plastically deformable non-limiting examples of such a material include stainless steel, titanium, tantalum and the like. In another preferred embodiment, the starting material may be one which expands via temperature-dependent memory (i.e., a material which when deformed will change back to its memory state upon reaching a certain temperature); non-limiting examples of such a material include nickel-titanium alloys (called for short "nitinol"), shape memory polymers, and the like. Alternatively, a material such as an elastic polymer may be used.

With reference to the accompanying Figures, there is illustrated a two-dimensional view of one embodiment of the present stent. Thus, the illustrated views are derived by unrolling into a flat plane a side elevation of a tubular stent.

The illustrated stent may be produced by any of a number of known techniques. For example, it is preferred to produce the present stent by starting with a hollow, unpatterned tube material (i.e., cylindrical wall with no porous surface) and then removing portions of the tube material to define a porous surface. While the precise nature of this processing is not particularly restricted, it is preferred to use a computer programmable, laser cutting system which operates by:

a. receiving the solid tube,
b. moving the solid tube longitudinally and rotationally under a laser beam to selectively remove sections of the solid tube thereby defining a porous surface; and
c. cutting stent sections of desirable length of the solid tube.

A suitable such laser cutting system is known in the art as the LPLS-100 Series Stent Cutting Machine. The operation of this system to produce the unexpanded stent is within the purview of a person skilled in the art.

Thus, the stent produced from the laser cutting system may be an unexpanded, expanded or intermediate state.

If desired, the stent material may have a coating material applied thereon. The coating material may be disposed continuously or discontinuously on the surface of the stent. Further, the coating may be disposed on the interior and/or the exterior surface(s) of the stent. The coating material may be one or more of a biologically inert material (e.g., to reduce the thrombogenicity of the stent) or a medicinal composition which leaches into the wall of the body passageway after implantation (e.g., to provide anticoagulant action, to deliver a pharmaceutical to the body passageway and the like)

The stent is preferably provided with a biocompatible coating, in order to minimize adverse interaction with the walls of the body vessel and/or with the liquid, usually blood, flowing through the vessel. The coating is preferably a polymeric material, which is generally provided by applying to the stent a solution or dispersion of preformed polymer in a solvent and removing the solvent. Non-polymeric coating material may alternatively be used. Suitable coating materials, for instance polymers, may be polytetraflouroethylene or silicone rubbers, or polyurethanes which are known to be biocompatible. Preferably, however, the polymer has zwitterionic pendant groups, generally ammonium phosphate ester groups, for instance phosphoryl choline groups or analogues thereof. Examples of suitable polymers are described in published International patent applications WOA-93/16479 and WO-A-93/15775. Polymers described in those specifications are hemo-compatible as well as generally biocompatible and, in addition, are lubricious. When a biocompatible coating is used, it is important to ensure that the surfaces of the stent are completely coated in order to minimize unfavourable interactions, for instance with blood, which might lead to thrombosis. Also, bio-absorbable materials such as high molecular weight poly-L-lactic acid can be used as part or all of the stent material.

This good coating can be achieved by suitable selection of coating conditions, such as coating solution viscosity, coating technique and/or solvent removal step. The coating, if present, can be applied to the stent in an expanded or contracted state.

Figure 1A:
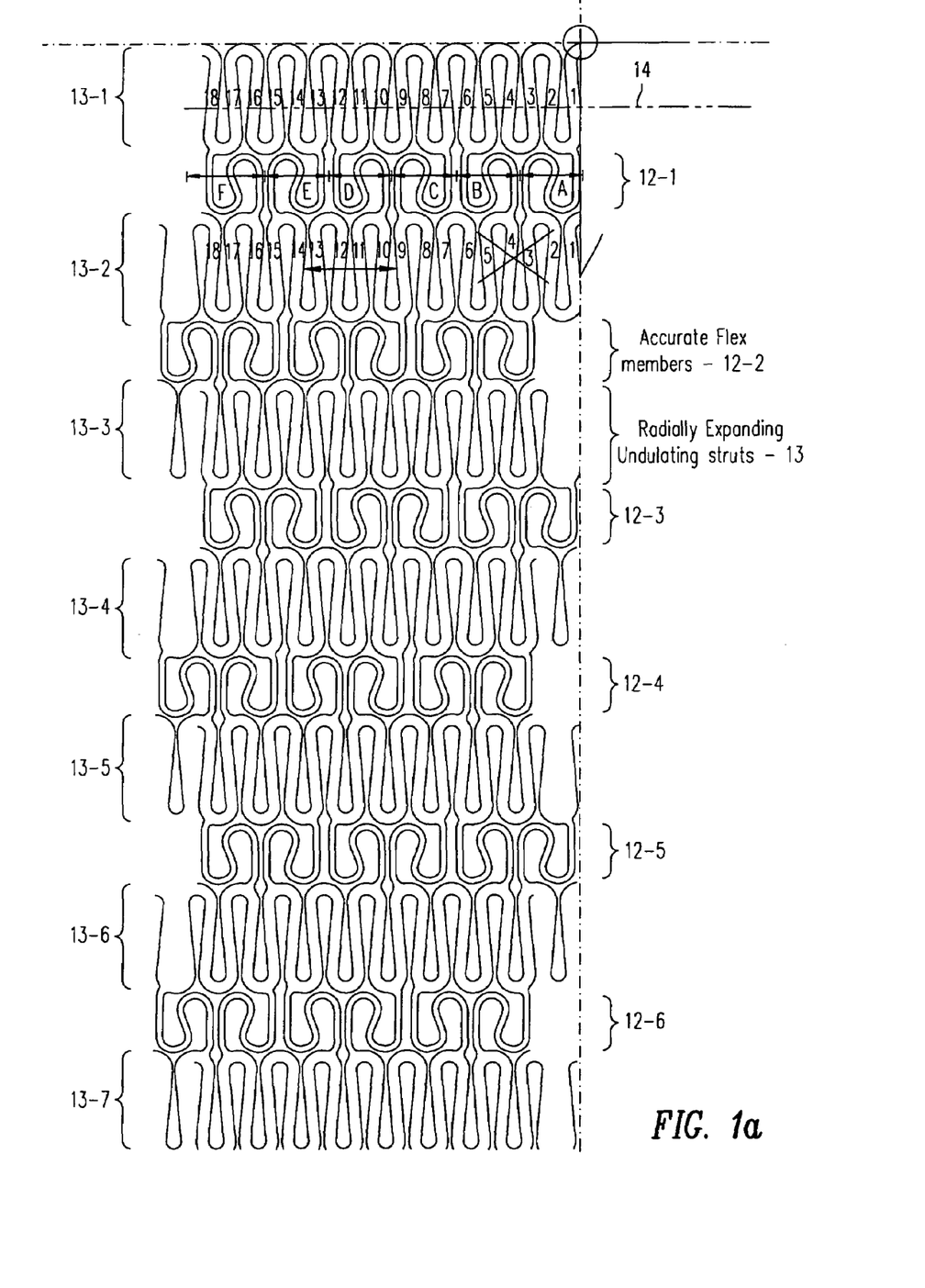
FIGS. 1a through 1h show the stent of this invention in various degrees of expansion after having been placed in a lumen or vessel.
Figure 1B:
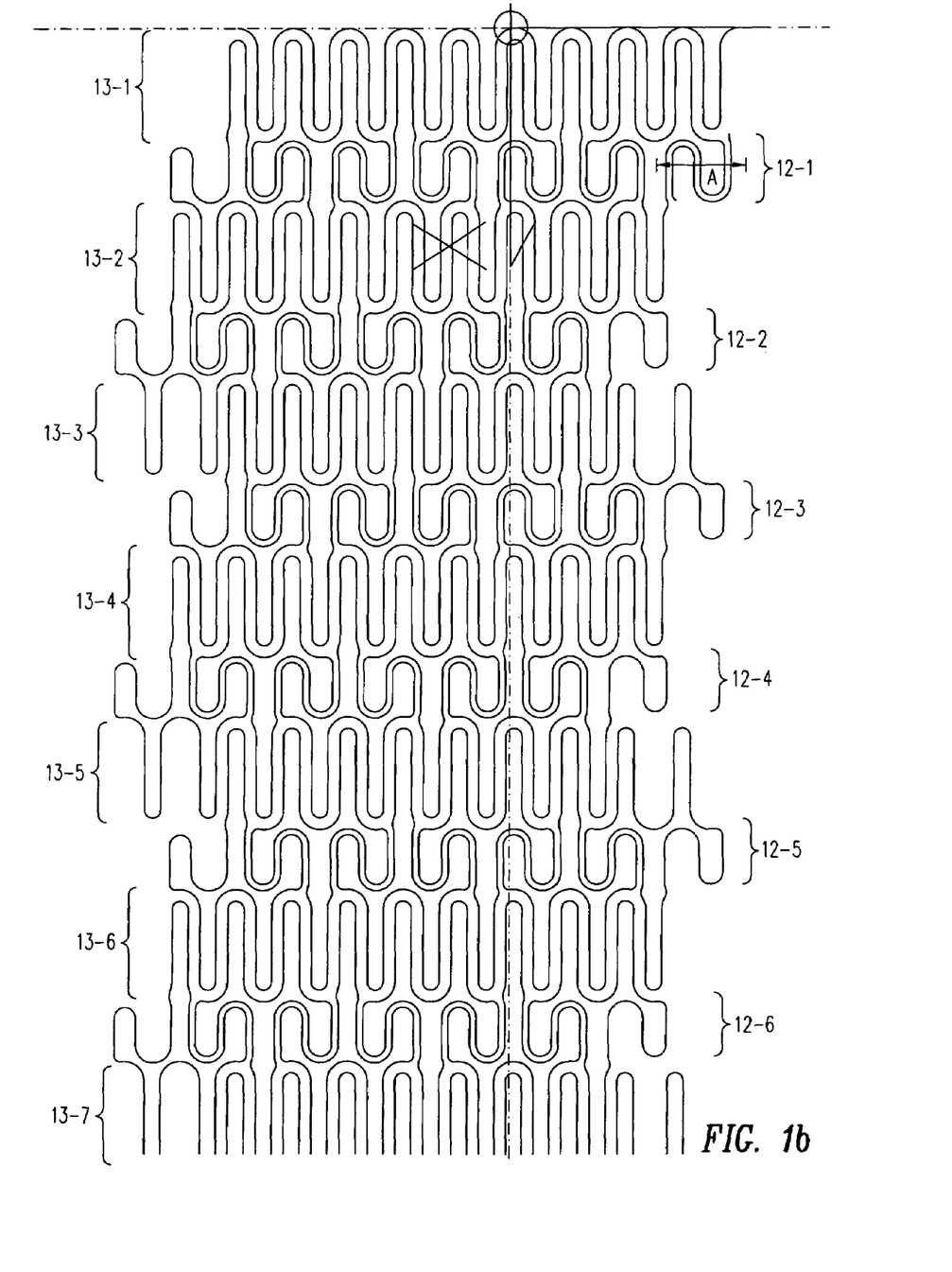
Figure 1C:
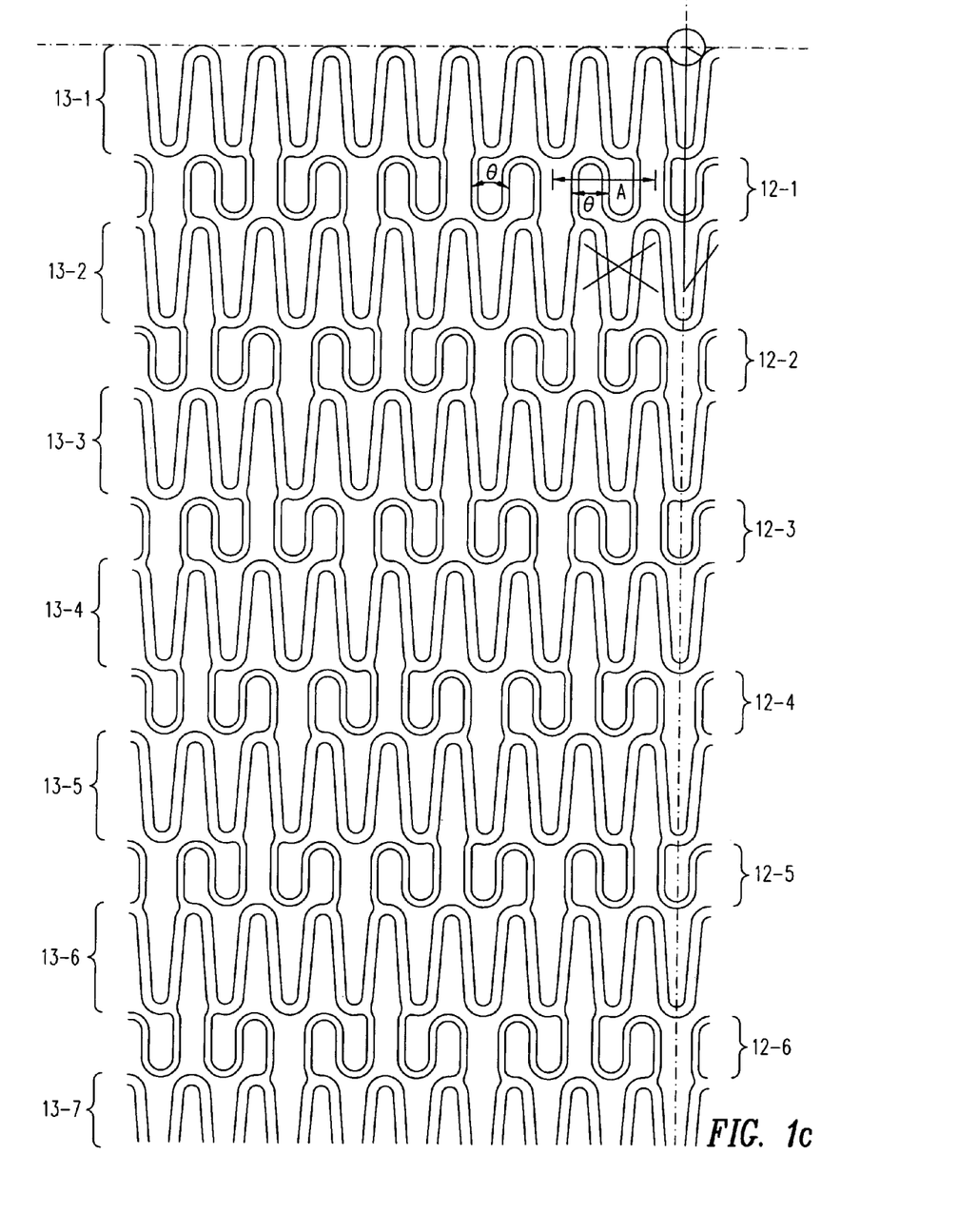
Figure 1D:
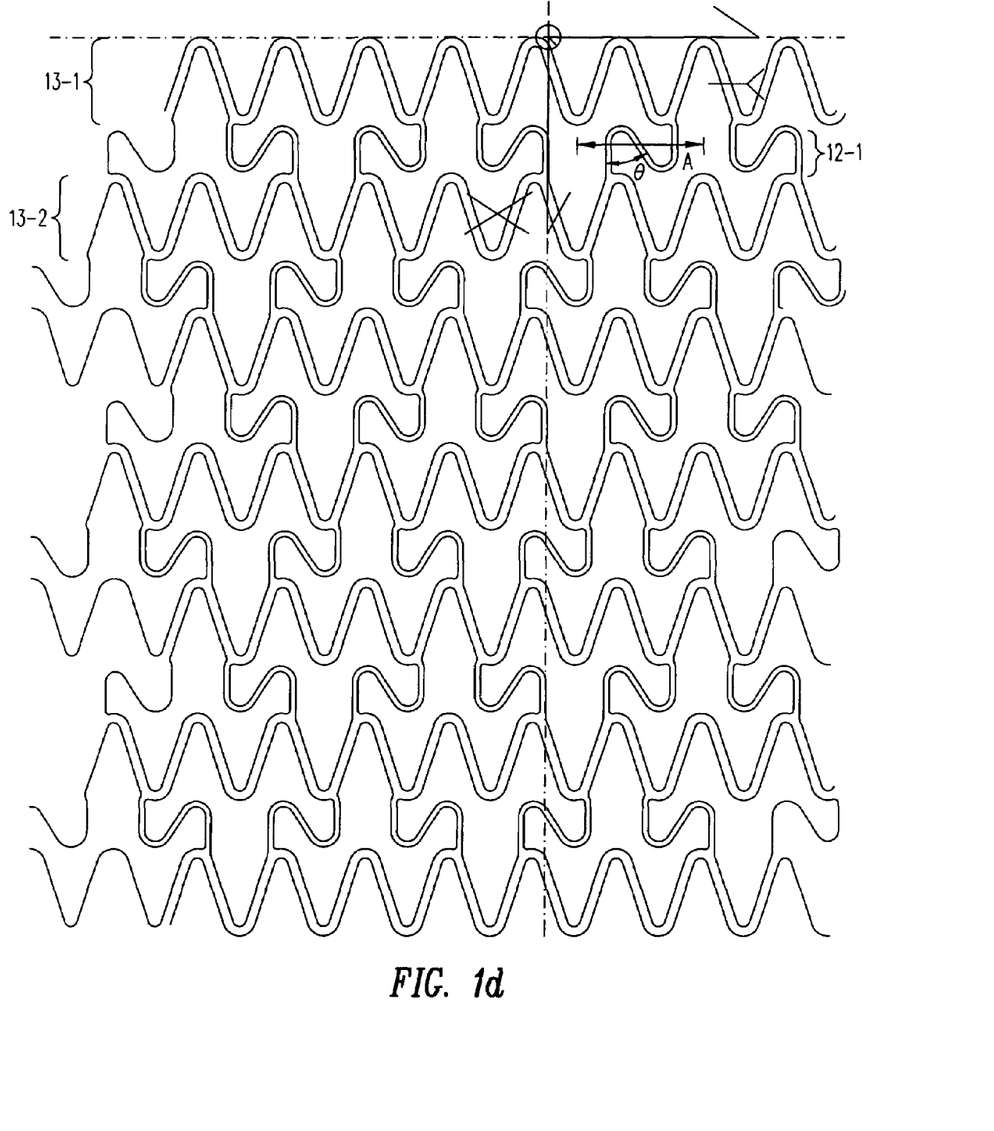

FIG. 1a illustrates in a plane the shape of the material which forms a stent in accordance with this invention. In the actual stent, the pattern shown in FIG. 1a is in a tubular form with the two edges of the material abutting. If the material in the tube was originally formed in a plane, then the material, after patterning, is rolled into a tubular form and the two abutting edges are welded to form the tube. Alternatively, as described above, the tube can be formed by taking a regular tube of continuous material and laser etching the tube under computer control to form the pattern shown in FIG. 1a. The stent structure in FIG. 1a has a plurality of radially expandable undulating rings 13-1 through 13-7, each ring containing a plurality of struts, with each directly adjacent pair of radially expandable undulating rings 13-$i$ and 13-(i+1) (where "i" is an integer varying from 1 on up) joined by a plurality of arcuate flex members 12-$i$A through 12-$i$F. Thus in FIG. 1a, the first radially expandable undulating ring 13-1 is connected by a plurality of arcuate flex members 12-1A through 12-1F to the second radially expandable undulating ring 13-2. Two characteristics of the undulating rings are of interest. First each undulating ring is made up of a plurality of U-shaped-bent sections with the arm of one U forming an arm of the adjacent oppositely facing U and with consecutive Us opening in opposite directions. The arms of each U are over-bent in the sense that in the sheathed or crimped condition (i.e., the smallest unexpanded condition) the ends of the arms furthest from the end section of the U (i.e., the "distal ends") are closer together than the ends of the arms directly attached to the end section of each U (i.e., the "proximal ends"). This over bending assists in allowing the radially expandable undulating ring to expand over a reasonable range without significantly shortening the stent. The end section of each "U" can be curved, flat, angled, pointed or any other appropriate shape. The tube from which the stent shown in FIG. 1a is formed may be any appropriate diameter and wall thickness.

Well known techniques can then be used to crimp the stent to its desired diameter for insertion into a vessel. In one embodiment, each radially expandable undulating ring can also be viewed as being made up of nine sinusoidal struts wherein each sinusoidal strut would start at the middle of an arm of a U and continue until it reaches the point where a second sinusoidal strut begins. Thus in FIG. 1a, a centerline 14 is shown through the center of radially expandable undulating ring 13-i and the intersection of centerline 14 with each arm of each U is identified with the numbers 1 through 18. From FIG. 1a, it is apparent that the first sinusoid is made up of a portion of the undulating ring extending from number 1 to number 3, the second sinusoid is made up of a portion of the undulating ring extending from 3 to 5, the third sinusoid is made up of a portion of the undulating ring extending from 5 to 7 and so on for a total of nine such sinusoids if the sinusoid extending from 18 to 1 is included when the material shown flat has been rolled into a tube.

Stents have a range of unexpanded diameters depending on their intended use.

Typically, unexpanded stents range in diameter from fractions of a millimeter on up.

The plurality of arcuate flex members (i.e., "links") connecting, for example, undulating ring 13-1 to undulating ring 13-2 comprises six such members as shown in FIG. 1a.

The arcuate flex section 12-1A extends from an end of arm 1 of the first sinusoidal strut in ring 13-1 through a sharp S-shape to the adjacent end of arm 3 of an undulating sinusoidal strut member shown in undulating ring 13-2. The arcuate flex member 12-1A (i.e, link A) in circumferential links 12-1 (illustrated by the flex member contained within the bracketed section A) is made up of the same material as the radially expandable undulating strut. This section A (as well as sections B, C, D, E, and F of links 12-1) expands circumferentially with expansion of the adjacent rings 13-1 and 13-2 while still holding the radially expandable undulating rings 13-1 and 13-2 in their correct places relative to the rest of the stent. The radial/circumferential expansion of the stent is accomplished over a substantial distance without longitudinally shrinking the stent because of the unique sinusoidal shape of the radially expandable undulating ring sections 13 and the compressed S-shapes of the arcuate flex members 12. Each other radially expandable undulating ring 13-i is joined to the adjacent radially expandable undulating rings 13-(i−1) and 13-(i+1) by arcuate flex members (12-(i−1) and 12-i (where i is an integer equal to 1 or greater). For example, circumferential links 12-1A through 12-iF connect rings 13-1 and 13-2. In links 12-1 through 12-6, each arcuate flex member is as described in connection with arcuate flex members 12-1A or 12-1B except that even numbered links 12-2, 12-4, 12-6 et al are circumferentially offset with respect to odd numbered links 12-1, 12-3, 12-5 et al. As a feature of this invention, adjacent pairs of arcuate flex members such as flex members 12-1A and 12-1B are mirrored. The mirroring of the links such as links 12-1A and 12-1B results in a closed unit cell. Any location within a cell has a minimum distance to the material defining the boundaries of the cell. The material defining the boundaries of the cell is made up of portions of the links such as 12-1A and 12-1B as well as portions of the strut materials from two adjacent undulating expansion rings.

Figure 1E:
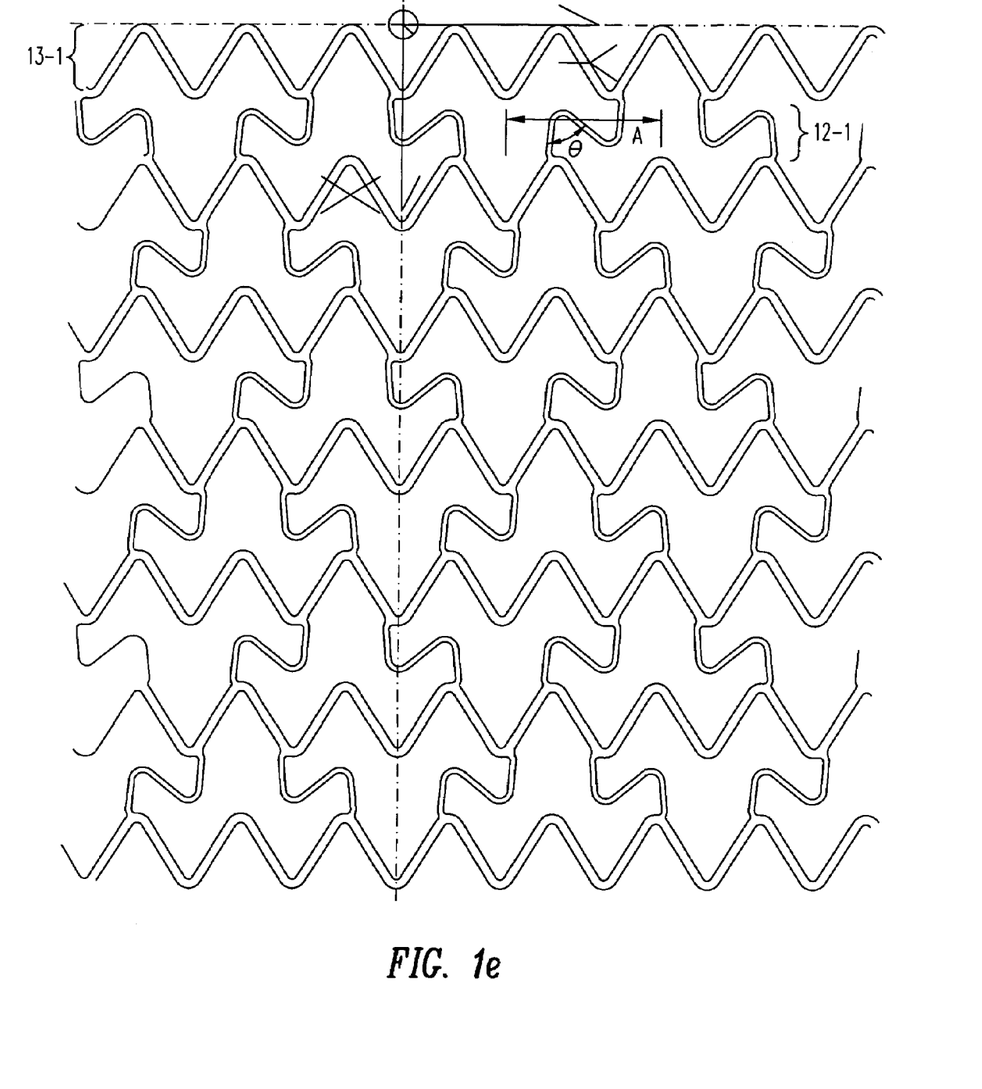
Figure 1F:
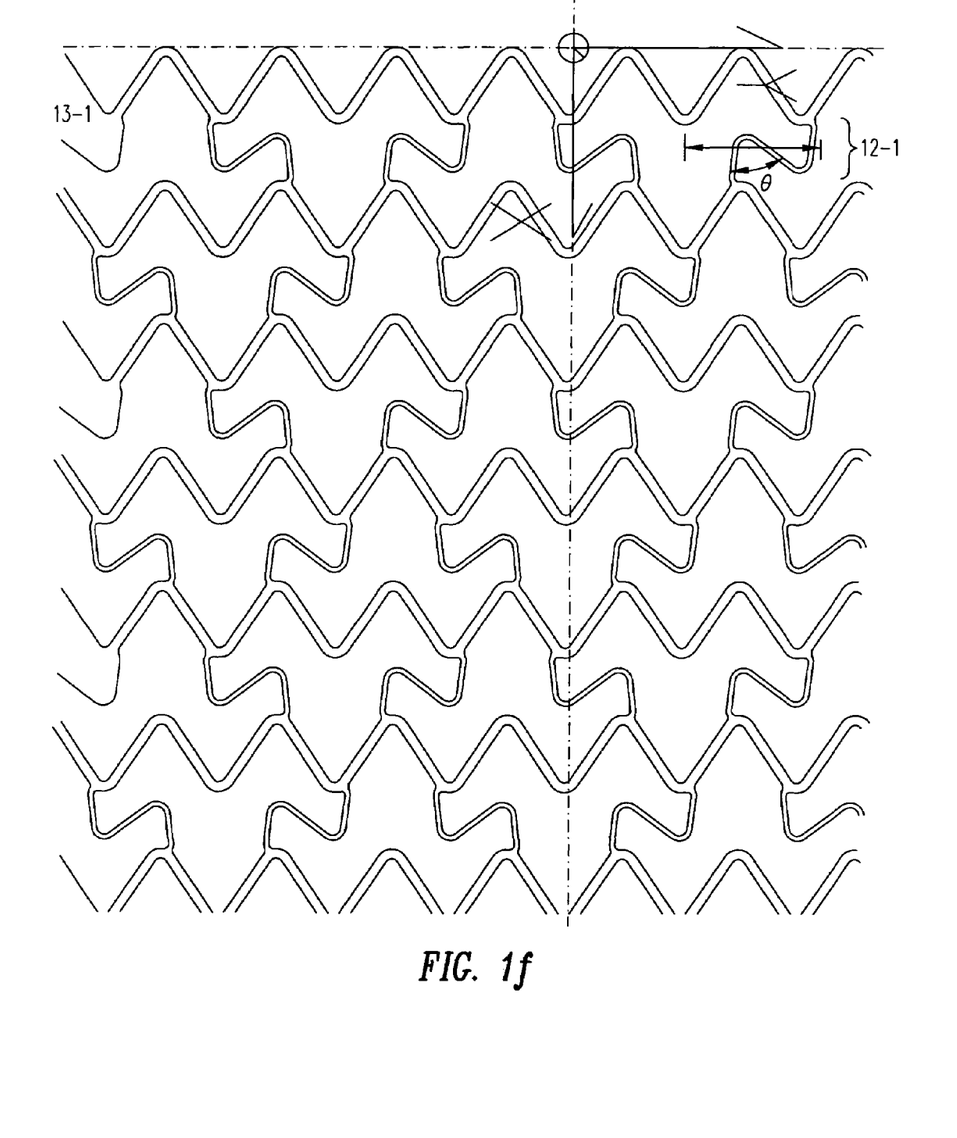
Figure 1G:
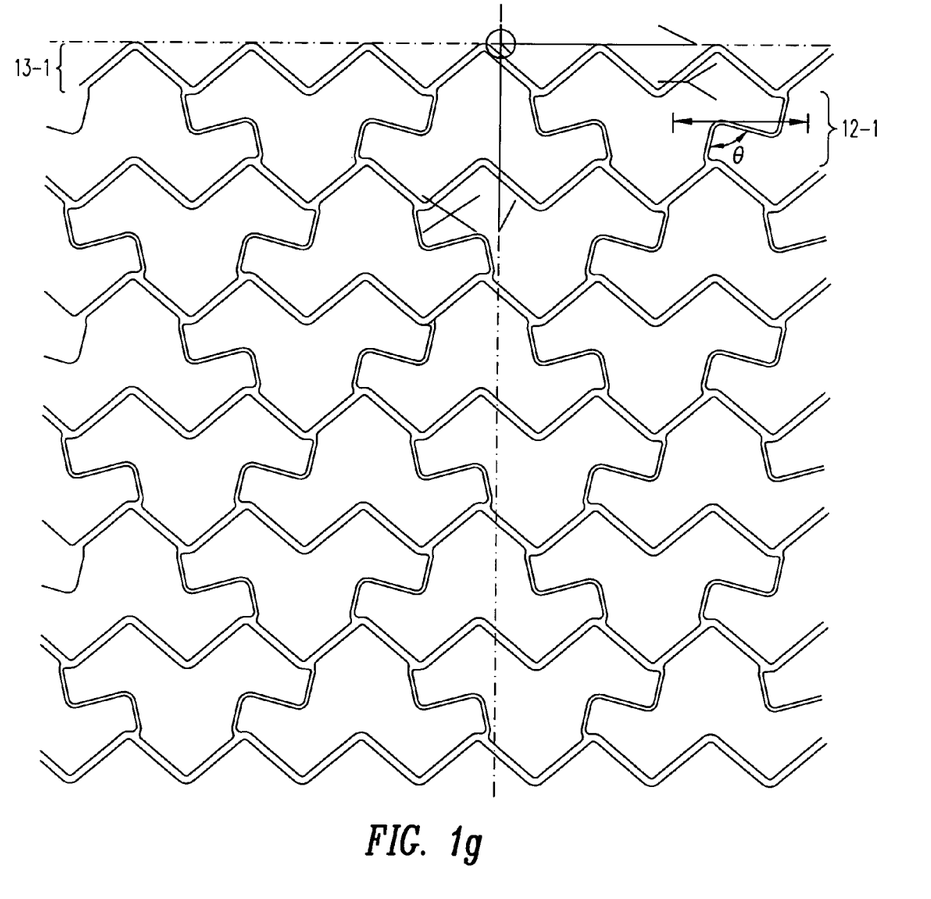
Figure 1H:
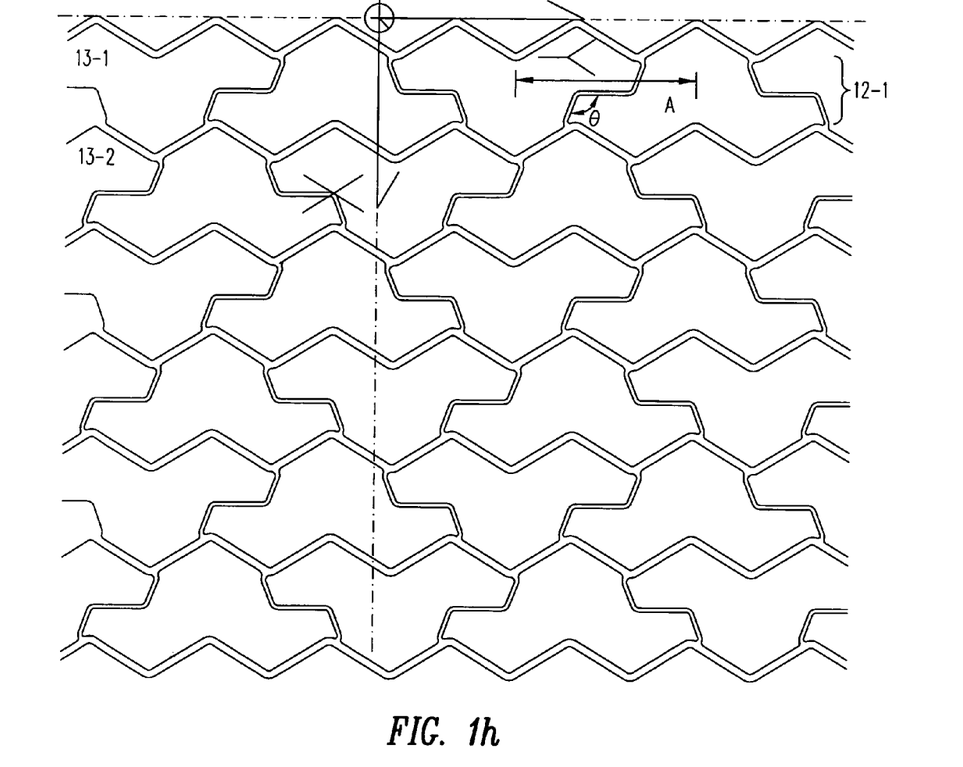

FIGS. 1b, 1c, 1d, 1e, if, 1g and 1h show the change in the shape of each radially expandable undulating ring 13 and the corresponding changes of the arcuate flex members 12 (i.e., links 12) connecting adjacent radially expandable undulating rings 13 as the stent is expanded to its full dimension. As can be seen by looking sequentially at FIGS. 1a to 1h, and focusing, for example, on radially expandable undulating ring 13-i and arcuate flex members 12-1, the arcuate flex members 12-1 extend longitudinally to connect adjacent radially expandable undulating rings such as rings 13-1 and 13-2 thereby to allow the stent to retain its approximate longitudinal length. The arcuate flex member 12-1A will be identified and labeled in each of FIGS. 1b through 1h. As can be seen from FIGS. 1b and 1c the dimension in the circumferential direction of circumferentially "S' shaped arcuate flex member 12-1A increases as the stent expands. This increase causes the flex member 12-1A to form an S with three parallel arms in FIG. 1b and with three arms forming small but definitely discernable acute angles 0 with each other in Fig. ic. Fig. id shows the three arms of the acute flex member 12-1A forming greater angles 0 of approximately 30° with each other. These angles 0 increase substantially as the stent is-expanded circumferentially. In FIG. 1e the angle A is approximately 45° and in Fig. if the angle A is approximately 60° In FIG. 1g the angle 0 approaches 90°. The arcuate flex member 12-1A in FIG. 1h has been expanded to such an extent that 0 is greater than 90°. The arcuate flex members represented, for example, by the members 12-1A through 12-1F, give to the stent flexibility during insertion into a lumen, conformability when expanded with and substantially uniform scaffolding.

In one embodiment of this invention the stent material can be a shape memory alloy such as nickel titanium (sometimes called "nitinol".) In fabricating a stent, the stent is placed in a heat source (at 200° C. to 600° C.) such as a salt bath or furnace for from one to thirty minutes to heat the stent material to establish its memory shape, to stress-relieve the stent, and to establish the active $Af^-$ (i.e., the temperature at which the material becomes entirely austenite at an appropriate temperature below body temperature such as 25°). Then the links are further heated locally to raise Af above the body temperature. Such heating can be done using a laser or by applying a voltage to the links for a short time (for example, 0.01 to 1.0 seconds) to raise the Af of the links to above the body temperature. This causes the link material to be predominantly or at least partially martensitic at body temperature (about 37° C.) or, for non-stent applications, at the minimum design temperature. The austenitic shape memory ring material has as its memory state the desired deployment diameter. This shape memory alloy is then compressed by, for example, crimping the stent and inserting the stent into a delivery sleeve to form the small unexpanded stent. The stent may be cooled into the martensitic phase before crimping. The stent is then placed in the human body. Upon removal of the sleeve when the stent is properly located in a lumen or vessel, the stent either has risen or will rise to the temperature of the body (typically 98.6° F.). This temperature is above the temperature at which the ring material changes from martensitic to austenitic and thus the stent will then expand naturally back to its original larger circumference thereby avoiding the need for using a balloon catheter.

The portions of the stent to be locally heat treated can be heated in as little as one tenth of a second using a laser or by treating each of these portions as a resistive wire. Optimum heating for the stent wire will be less than one second, such as one half second or less. This prevents undesirable heating of adjacent portions of the stent. In the austenitic phase the material assumes a given position. The austenitic material,' when chilled, changes to a martensitic phase but retains the shape it had in the austenitic phase. The martensitic material can then be crimped, compressed, placed in a sleeve and inserted into a human vessel. When the sleeve is removed, the material has risen in temperature, becomes austenitic and returns to its normal memory position. By appropriately selecting and treating the material to have a transition temperature to the austenitic phase at a suitable interval below the body temperature, a stent can be fabricated which expands upon reaching a body temperature to hold open a vessel or other body part.

Applying additional local heat treatment has the effect of elevating the transformation temperature $A_f$. If the $A_f$ of a portion of the device is above body temperature, then that portion will be at least partially in the martensitic phase. This portion will not be superelastic at the design temperature and thus will not spring back to its memory state. As a result, this portion can be easily deformed with less force than an identical portion in the austenitic condition. This behavior, when established in a stent link, enhances the flexibility and conformability of the stent. In superelastic stents, there is a common trade-off between flexibility/conformability and scaffolding/drug delivery because superelastic links do not deform easily. By heat-treating the links to be martensitic at body temperature, this trade-off can be improved; i.e., more links can be used without sacrificing flexibility/conformability.

Figure 2A:
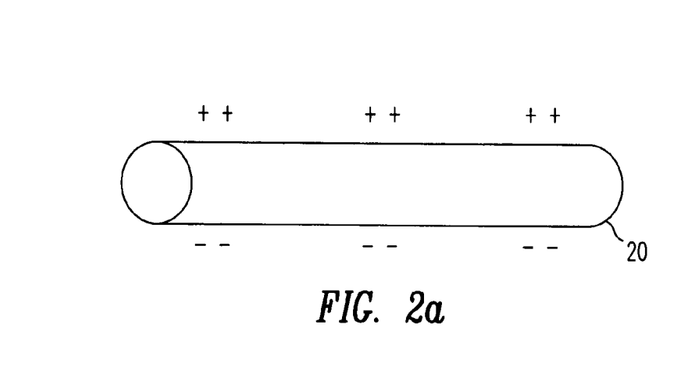
FIGS. 2a, 2b, 2c and 2d show various techniques for changing the phase transformation properties of selected portions of the cylindrical stent.

FIG. 2a shows a cylindrical stent having applied thereto positive and negative electrical contacts thereby to cause electrical current to flow through the portions of the stent material between the positive and negative contacts. The current flow heats the stent material such that the material changes from martensitic to austenitic.

Figure 2B:
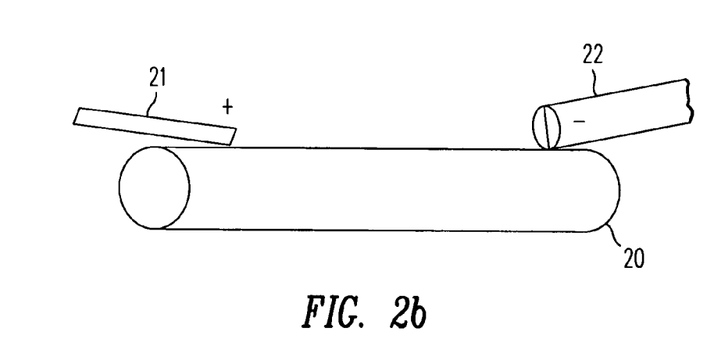

FIG. 2b shows a positive electrode 21 and a negative electrode 22 applied along the longitudinal axis of the stent to cause the stent material between the two contacts to change in phase from martensitic to austenitic.

Figure 2C:
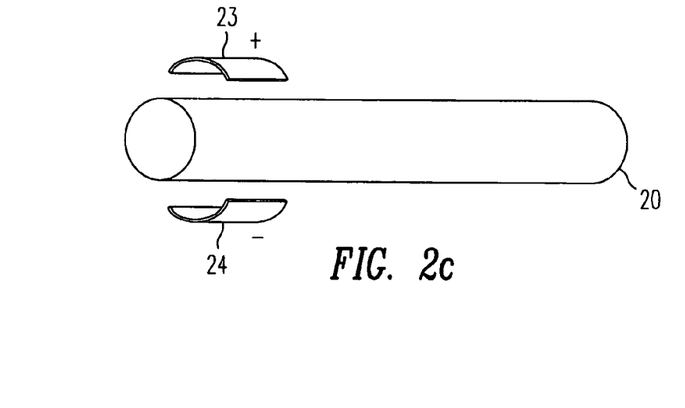

FIG. 2c shows a curved electrode 23 of positive polarity capable of being placed onto a portion of the stent to be converted from martensitic to austenitic. A corresponding curved electrode 24 of negative polarity likewise capable of being placed on the cylindrical stent material to be converted from martensitic to austenitic is shown below the stent 20.

Figure 2D:
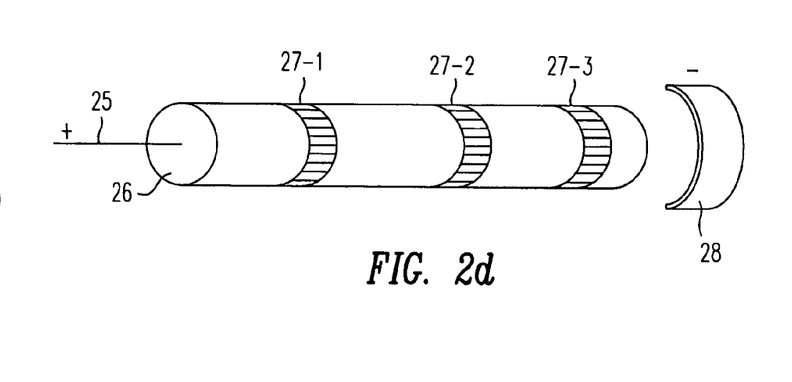

FIG. 2d shows a ceramic cylinder 26 having a conductive wire 25 intended to carry a positive voltage running longitudinally along the length of the ceramic cylinder 26. Conductive wire 25 makes electrical contact to electrically conductive portions 27-1, 27-2 and 27-3 of conductive material on the surface of ceramic cylinder 26. Cylinder 26 is placed in a stent and then an electrode 28 intended to carry a negative voltage is applied over the portions of the stent material to be locally heat treated. Electrical current is then passed through the lead 25 to the corresponding positive electrode such as 27-1 and the current then flows through the portions of the stent material to be locally heat treated to negative electrode 28 placed directly adjacent and in contact with these portions of stent material.

Other structures for appropriately applying electrical current to those portions of the stent material to be converted from martensitic to austenitic will be apparent in view of this disclosure.

Also, a laser for this purpose can be used in the manner disclosed in a paper entitled "Laser Annealing Of Shape Memory Alloys: A Versatile Tool For Developing Smart Micro-devices" by Y. Bellouard et al., published in the Journal of Physics IV France 11 (2001), Pr8-571. See also "Local Annealing Of Complex Mechanical Devices: A New Approach For Developing Monolithic Micro-devices" by Y. Bellouard et al., published by Materials Science And Engineering A273-275 (1999) 795-798.

FIGS. 3a, 3b, 3c and 3d illustrate cells associated with the stent of this invention (FIG. 3a) and three prior art stents as well as isomers representing all points having the same minimum distances from the cell boundaries.

A parameter of importance in determining the performance of a cell is the minimum distance from a point within each cell to the closest wall of the cell. A series of isomers, each isomer representing the points having a given minimum distance from a cell wall, can be drawn. Thus each isomer represents all points having the same minimum distance to the closest adjacent portion of the strut or link forming the boundaries of the cell. When a series of isomers have been drawn within a cell, there is a point which is further from the cell boundaries than all other points in the cell. This point is called the "least supported point" (hereinafter "LSP"). In the stent of this invention, the distance from the LSP to the nearest cell boundary (i.e., to the strut and link materials surrounding the cell) has a smaller such maximum than the LSP in prior art cells. In other words, there is a point on the vessel wall within each cell that is least well supported compared to all other points on the vessel wall within the cell. However, as is apparent from FIG. 1h, the material making up the stent of this invention is reasonably uniformly distributed over the surface of the vessel when expanded. This means that the scaffolding performance of the invented stent as well as the drug distribution capability of this stent will be enhanced relative to a stent of the prior art.

While some stents are described in terms of "percent metal coverage" (and this is a useful parameter), one problem with this measure is that a stent with a few bulky struts will have the same percent metal coverage as a stent with many lightweight struts. However, in the areas of vessel wall support and drug delivery, the performance of the two stents will differ significantly. Since various architectures distribute the same metal in dramatically different ways, thereby rendering different results in terms of vessel wall support and drug delivery, the issue is how the metal in the stent is deployed and used. Optimal use of the metal affects drug delivery, vessel wall support, insertability of the stent into the vessel and the life of stent.

An optimal stent will restore optimal blood flow through the vessel and provide radial support while at the same time minimizing vessel injury during insertion and expansion and minimizing tissue prolapse. Such a stent will maintain patency and optimize delivery of drugs. In order to determine how successful the stent will be in radially supporting the vessel wall, the size of the holes between the struts and within the boundary of a cell must be determined. Since all cells have different shapes, the ability of a given cell to support tissue is the issue. As described briefly above, every cell is such that there is a point (the "LSP") within the cell farthest away from the closest cell boundary or strut (i.e., further away from the closest point on the cell boundary). Every other point on the vessel wall is supported by a closer strut than FIGS. 3b, 3c and 3d, the distance from the least-supported point in the vessel wall to the nearest strut in the stent of this invention is 0.0168 inches. The distances of the least supported points in the vessel wall to the nearest strut in the cells of FIGS. 3b, 3c and 3d are 0.0236 inches, 0.0254 inches and 0.0204 inches, respectively. Thus the stent of this invention has a cell which is more efficient in supporting the vessel wall and thus provides better scaffolding and more uniform drug delivery than these other prior art cells shown in FIGS. 3b, 3c, and 3d.

Figure 3A:
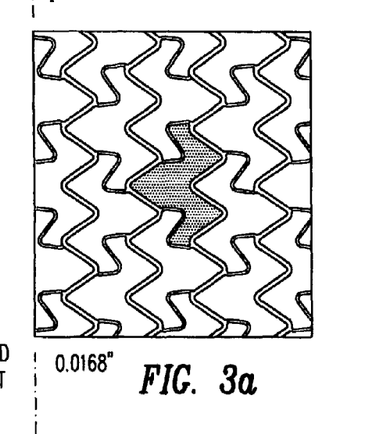
FIGS. 3a, 3b, 3c and 3d illustrate isomers associated with the stent cell of this invention and three prior art stent cells, respectively, and show in inches the minimum distance of the point that is farthest from the stent boundary for the stent cell of this invention and for three (3) prior art stent cells respectively.
Figure 3B:
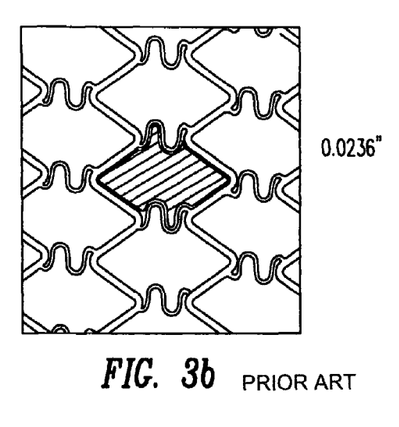
Figure 3C:
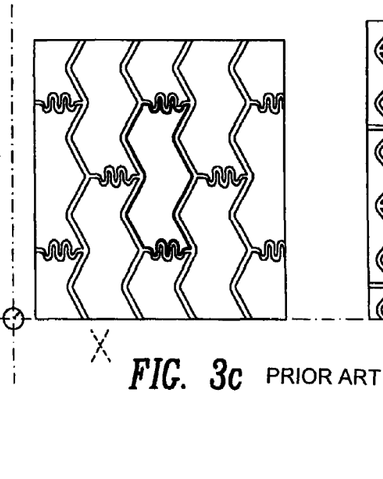
Figure 3D:
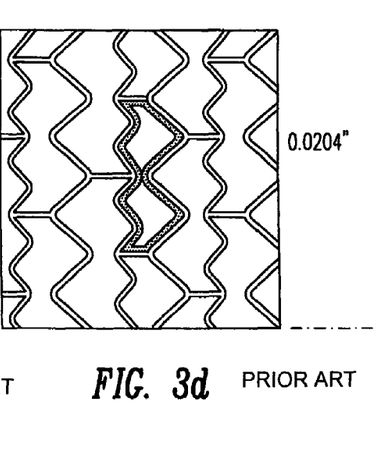

In the cell of this invention shown in FIG. 3a, the isomers generally cover the whole area of the stent leaving very few places enclosed by the first isomer to touch itself. In FIG. 3b, a prior art stent has isomers but many of the isomers do not extend into a number of the boundary protrusions defining the cell area indicating that this cell will provide a very high dosage of drugs in these areas if 'the stent is coated with a drug for timed release into the vessel.

The cell of FIG. 3c has the same problem as the cell of FIG. 3b because of the boundary protrusions defining the cell area. These protrusions reflect the very tight coupling of the linkage between the circumferentially expanded wires associated with the stent.

The cell of FIG. 3d avoids the protrusions of the cells of FIGS. 3b and 3c but has large areas of vessel wall less well supported when compared to the support offered by the cell of this invention. Thus the cell of FIG. 3d has a number of isomers but the isomer which doubles back and touches itself leaves within its boundaries two large areas having no continuous isomer extending throughout the whole cell. Thus this cell has relatively poor scaffolding and drug delivery.

The isomers represent a contour much as in contour lines on a topographical map. When one of these isomers or contour lines offset from the cell parameter touches itself, the area bound by that contour is a measure of how the struts are distributed around the cell area. The cell of this invention shown in FIG. 3a, when expanded to 3 mm diameter, has an area of 0.00093 inch$^2$ bound by the contour which touches itself. The cell in FIG. 3b has an area of .00427 inch$^2$ 'bound by the contour that touches itself. The cell in FIG. 3c has an area of 0.00562 inch$^2$ bound by the contour which first touches itself and the cell in FIG. 3d has an area of 0.00267 inch$^2$ within the contour which first touches itself. The area within the contour which touches itself is a measure of how efficiently the stent will support the vessel walls and of how uniformly any drugs coating the strut material will be distributed along the vessel wall. As can be seen from this comparison, the cell of this invention has the smallest area surrounded by the contour which touches itself. This means that this cell provides better scaffolding and drug delivery than the prior art cells shown.

In order to optimize the antirestenosis therapy, uniform or "even" delivery of drug to the vessel wall is desirable. The point at which a contour or isomer bumps into itself can be considered a point at which the tissue in the vessel wall is getting a "double" dose of drugs. The smaller the area left inside the contour which first bumps into itself the better because this means that there is less area on the vessel wall supported by the stent which would get a low or inadequate distribution of drug. To the extent this area is left with too low a dosage or drug or without any drug (i.e., left untreated) this area must be minimized. The cell of this invention minimizes this area compared to the cells of the prior art of FIGS. 3b and 3d. With respect to the cells of FIGS. 3b and 3c, the cell of this invention minimizes regions of the vessel wall which will receive drug overdoses.

A further measure of the performance of a stent is the ratio of a cell's perimeter to its internal area. This parameter, which has dimensions of "1/inch" has a value of 109.8 for the cell of one embodiment of this invention expanded to a stent diameter of 3 mm. On the other hand, the cells of FIGS. 3b, 3c, and 3d have ratios of cell perimeters to internal area of 88.4 per inch, 78.5 per inch, and 85.6 per inch, respectively. Therefore the cell of this invention when fully expanded gives more scaffolding per unit area of vessel wall to be supported than do the prior art cells shown in FIGS. 3b, 3c, and 3d.

The parameters of the FIG. 3a cell of this invention are shown in Table 1 along with the corresponding parameters of three prior art cells.

TABLE 1

| Cell | Distance from least-supported point in vessel wall to nearest strut (inches) | Ratio of cell's perimeter to its internal area (in/in$^2$~) | The area bounded by that contour offset from the cell perimeter |
|---|---|---|---|
| FIG. 3a | 0.0168 | 109.8 | 9.3 |
| FIG. 3b | 0.0236 | 88.4 | 42.7 |
| FIG. 3c | 0.0254 | 78.50 | 56.2 |
| FIG. 3d | 0.0204 | 85.6 | 26.7 |

While this invention has been described with reference to illustrative embodiments and examples, the description is not intended to be limiting. Thus, various modifications of the illustrative embodiments, as well as other embodiments of the invention, will be apparent to persons skilled in the art in view of this description. It is therefore contemplated that the appended claims will cover any such modifications or embodiments.

All publications, patents and patent applications referred to herein are incorporated by reference in-their entirety to the same extent as if each individual publication, patent or patent application was specifically and individually indicated to be incorporated by reference in its entirety.

What is claimed is:

1. A stent comprising:
   a first radially expandable undulating ring comprising a first apex and a second apex;
   a second radially expandable undulating ring adjacent to the first radially expandable undulating ring, the second radially expandable undulating ring comprising a third apex and a fourth apex circumferentially offset with respect to the first and second apices;
   a mirrored pair of first and second flex members wherein the first flex member, having only two connection locations, is connected to the first apex at a first connection location and to the third apex at a third connection location, and the second flex member, having only two connection locations, is connected to the second apex at a second connection location and to the fourth apex at a fourth connection location;
   wherein in adjacent radially expandable undulating rings, apices that are circumferentially aligned point in the same direction.

2. The stent of claim 1, wherein the first radially expandable undulating ring and the second radially expandable undulating ring are connected by a plurality of flex members.

3. The stent of claim 2, wherein a portion of the first radially expandable undulating ring between the first and second connection locations comprises more than one complete sinusoidal cycle.

4. The stent of claim 2, wherein a portion of the second radially expandable undulating ring between the third and fourth connection locations comprises less than one complete sinusoidal cycle.

5. The stent of claim 2, wherein: (i) a portion of the first radially expandable undulating ring between the first and second connection locations comprises more than one complete sinusoidal cycle, and (ii) a portion of the second radially expandable undulating ring between the third and fourth connection locations comprises less than one complete sinusoidal cycle.

6. The stent of claim 1, wherein the flex members include arcuate portions.

7. The stent of claim 1, wherein the flex members comprise S-shaped members.

8. The stent of claim 7, wherein the S-shaped members comprise a fifth apex in substantial circumferential alignment with apices of the first and second radially expandable undulating rings.

9. The stent of claim 8, wherein the S-shaped members further comprise a sixth apex in substantial circumferential alignment with apices of the first and second radially expandable undulating rings.

10. The stent of claim 7, wherein the S-shaped members comprise a fifth apex and a sixth apex, and further wherein each of the fifth and sixth apices of the S-shaped members are in substantial circumferential alignment with apices of the first and second radially expandable undulating rings.

11. The stent of claim 1, further comprising a biocompatible surface treatment or coating thereon.

12. The stent of claim 1, further comprising a medicinal agent included in or applied to the surface of the radially expandable undulating rings and the flex members.

13. The stent of claim 1, wherein the radially expandable undulating rings and flex members are constructed of a material, and further wherein an expansion of said stent to a deployment diameter involves substantially plastic deformation.

14. The stent of claim 1, wherein the radially expandable undulating rings and the flex members are constructed of a material wherein an expansion of said stent to a deployment diameter involves substantially elastic deformation.

15. The stent of claim 1, wherein the first radially expandable undulating ring, the second radially expandable undulating ring and the flex members comprise stainless steel.

16. The stent of claim 1, wherein the first radially expandable undulating ring, the second radially expandable undulating ring and the flex members comprise a shape memory material.

17. The stent of claim 1, wherein the first radially expandable undulating ring, the second radially expandable undulating ring and the flex members comprise nitinol.

18. The stent of claim 1, wherein the first and second radially expandable undulating rings and the mirrored pair of first and second flex members comprise a bio-absorbable material.

19. The stent of claim 18, wherein said bio-absorbable material is poly-L-lactic acid.

20. A stent comprising:
a first radially expandable undulating ring having a diameter of a first magnitude, comprising a first apex and a second apex;
a second radially expandable undulating ring adjacent to the first radially expandable undulating ring, the second radially expandable undulating ring having a diameter of a second magnitude equal to the first magnitude and comprising a third apex and a fourth apex;
first and second flex members, wherein the first flex member, having only two connection locations, is connected to the first apex at a first connection location and to the third apex at a third connection location, and the second flex member, having only two connection locations, is connected to the second apex at a second connection location and to the fourth apex at a fourth connection location;
wherein a circumferential distance between the first connection location and the second connection location is a first magnitude and a circumferential distance between the third connection location and the fourth connection location is a second, lesser magnitude and further wherein in adjacent radially expandable undulating rings apices that are circumferentially aligned point in the same direction.

21. The stent of claim 20, wherein the first radially expandable undulating ring and the second radially expandable undulating ring are connected by a plurality of flex members.

22. The stent of claim 21, wherein a portion of the first radially expandable undulating ring between the first and second connection locations comprises more than one complete sinusoidal cycle.

23. The stent of claim 21, wherein a portion of the second radially expandable undulating ring between the third and fourth connection locations comprises less than one complete sinusoidal cycle.

24. The stent of claim 20, wherein: (i) a portion of the first radially expandable undulating ring between the first and second connection locations comprises more than one complete sinusoidal cycle, and (ii) a portion of the second radially expandable undulating ring between the third and fourth connection locations comprises less than one complete sinusoidal cycle.

25. The stent of claim 20, wherein the flex members include arcuate portions.

26. The stent of claim 20, wherein the flex members comprise S-shaped members.

27. The stent of claim 26, wherein the S-shaped members comprise a fifth apex in substantial circumferential alignment with apices of the first and second radially expandable undulating rings.

28. The stent of claim 27, wherein the S-shaped members further comprise a sixth apex in substantial circumferential alignment with apices of the first and second radially expandable undulating rings.

29. The stent of claim 26, wherein the S-shaped members comprise a fifth apex and a sixth apex, and further wherein each of the fifth and sixth apices of the S-shaped members are in substantial circumferential alignment with apices of the first and second radially expandable undulating rings.

30. The stent of claim 20, wherein the first and second flex members comprise a mirrored pair.

31. The stent of claim 20, further comprising a biocompatible surface treatment or coating thereon.

32. The stent of claim 20, further comprising a medicinal agent included in or applied to the surface of the radially expandable undulating rings and the flex members.

33. The stent of claim 20, wherein the radially expandable undulating rings and flex members are constructed of a material, and further wherein an expansion of said stent to a deployment diameter involves substantially plastic deformation.

34. The stent of claim 20, wherein the radially expandable undulating rings and the flex members are constructed of a material wherein an expansion of said stent to a deployment diameter involves substantially elastic deformation.

35. The stent of claim 20, wherein the first radially expandable undulating ring, the second radially expandable undulating ring and the flex members comprise stainless steel.

36. The stent of claim 20, wherein the first radially expandable undulating ring, the second radially expandable undulating ring and the flex members comprise a shape memory material.

37. The stent of claim 20, wherein the first radially expandable undulating ring, the second radially expandable undulating ring and the flex members comprise nitinol.

38. The stent of claim 20, wherein the first and second radially expandable undulating rings and the first and second flex members comprise a bio-absorable material.

39. The stent of claim 38, wherein said bio-absorbable material is poly-L-lactic acid.

40. The stent of claim 1 wherein the distance between the first connection location and the second connection location is greater than the distance between the third connection location and the fourth connection location.

41. The stent of claim 1 wherein the distance between the first connection location and the second connection location is less than the distance between the third connection location and the fourth connection location.

* * * * *